United States Patent [19]

Autant et al.

[11] Patent Number: 5,290,560

[45] Date of Patent: Mar. 1, 1994

[54] EXTRUSION OF AN ADMIXTURE OF A MELTABLE BINDER AND A FOOD OR DRUG

[75] Inventors: Pierre Autant, Commentry; Jacques Ruel, Saint-Gratien, both of France; Stephen Weinhold; Charles A. McCombs, both of Kingsport, Tenn.; Ernest P. Smith, Blountville, Tenn.; Stephen H. Wu; Louis P. Hoskins, both of Kingsport, Tenn.

[73] Assignee: Rhone-Poulenc Nutrition Animale, Commentry, France

[21] Appl. No.: 719,039

[22] Filed: Jun. 21, 1991

[30] Foreign Application Priority Data

Jun. 29, 1990 [FR] France .................. 90 08280

[51] Int. Cl.$^5$ ................................ A23K 1/00
[52] U.S. Cl. ..................... 424/438; 424/484; 424/486; 424/489; 424/501; 424/502; 426/96; 426/807
[58] Field of Search .............. 424/438, 484, 486, 489, 424/501, 502; 426/96, 807

[56] References Cited

U.S. PATENT DOCUMENTS

| | | | |
|---|---|---|---|
| 3,655,864 | 4/1972 | Grass, Jr. ................ | 424/438 |
| 3,880,990 | 4/1975 | Bauer et al. ............. | 424/438 |
| 4,181,708 | 1/1980 | Dannelly .................. | 424/482 |
| 4,181,709 | 1/1980 | Dannelly ................. | 424/482 X |
| 4,181,710 | 1/1980 | Dannelly .................. | 424/482 |
| 4,713,245 | 12/1987 | Ando et al. ............... | 424/438 |
| 4,842,863 | 6/1989 | Nishimura et al. ......... | 424/438 |
| 4,876,097 | 10/1989 | Autant et al. ............. | 426/74 |
| 4,877,621 | 10/1989 | Ardaillon et al. .......... | 424/438 X |
| 4,948,589 | 8/1990 | Iijima et al. .............. | 424/438 |
| 5,098,718 | 3/1992 | Ardaillon et al. .......... | 424/438 X |

Primary Examiner—Thurman K. Page
Assistant Examiner—Robert H. Harrison
Attorney, Agent, or Firm—Finnegan, Henderson, Farabow, Garrett & Dunner

[57] ABSTRACT

The present invention relates to new granules, as well as the process for their preparation, obtained by extrusion of a mixture containing a meltable binder in an amount such that it permits the passage of the mixture through a die. The granules obtained are then coated with a polymer permitting their trans-rumen passage without degradation. After coating, these granules are used for animal feeding of ruminants.

9 Claims, No Drawings

EXTRUSION OF AN ADMIXTURE OF A MELTABLE BINDER AND A FOOD OR DRUG

The present invention relates to a process for the preparation of granules of active principles. It relates more particularly to a process for the preparation of granules of active principles intended for the feeding or treatment of ruminants.

It is known, for example according to U.S. Pat. Nos. 4,181,708, 4,181,709 and 4,181,710, to prepare granules, suitable for administration to ruminants, composed of a core of active substance and a coating based on a hydrophobic substance and a polymer resistant to the neutral pH of the rumen and degradable at the more acid pH of the abomasum.

The core of these granules, composed of the active principle, is in granular form. It is obtained by dry mixing of the active substances and one or more binders, if appropriate with neutralizing agents, which mixture is then wetted by adding 10 to 20% of water and converted to a pasty mass, which is granulated by extrusion at ambient temperature and converting to spheres. The moist granules are dried in an oven or a fluidised bed.

When the moist mass is used as described in the abovementioned patents, the granules obtained after extrusion and converting to spheres never have a perfectly spherical form after drying but always have surface roughness or irregularities and a high porosity, which make the subsequent coating operation more compelling.

This coating operation is carried out, again in accordance with the abovementioned patents, directly on the granules obtained after drying using the mixture of polymer and hydrophobic substances. This coating mixture is dissolved in an organic solvent and then sprayed on the granules.

In order to obtain a correct protection of the active principle, it is necessary to spray at least 25 g of the polymer and fatty acid mixture per 100 g of granulated active substance, and the coating layer has a thickness of about 150 mm (see Example 1 of U.S. Pat. No. 4,181,710).

The present invention has sought to avoid the extrusion of a moist mixture to prepare the active principle cores. This objective has been achieved by using a granule having been prepared by extrusion of a mixture containing a binder in the molten state as active principle core before undergoing coating. This active principle core is obtained by extrusion of a mixture containing the active principles, preferably in the solid state, and a meltable binder in an amount sufficient to allow the passage through a die. This amount is preferably less than 25% by weight of the mass of the granules.

The meltable binder used is preferably a polyethylene wax, a paraffin, an oil or an optionally hydrogenated animal fat, a fatty acid containing 10 to 32 carbon atoms, the corresponding esters or alcohols and very particularly stearic acid. In fact, the latter has the advantage of being a foodstuffs product and one of the preferred constituents of the coating layer.

In order to prevent exudation of the binder during the extrusion, it is frequently advantageous to add a polymer to the mass, which polymer is preferably soluble in the binder, such as the polymers based on vinylpyridine and styrene, alkylcellulose (ethylcellulose), hydroxyalkylcellulose (hydroxypropylcellulose), polyvinylpyrrolidone or the polyethylenes. It is very particularly preferred to use the copolymer based on vinylpyridine and styrene which also serves for the coating layer, or ethylcellulose.

In order to increase the density of the granule, it is sometimes advantageous to add a filler chosen from the inorganic fillers (silica, talc).

The preferred composition by weight for forming the core of the granules is as follows:

| | |
|---|---|
| Active principles | 95 to 80% |
| Meltable binder | 5 to 20% |
| Polymer less than or equal to | 2%. |

An even more preferential composition consists of:

| | |
|---|---|
| Active principles | 90 to 84% |
| Meltable binder | 10 to 16% |
| Polymer less than or equal to | 1%. |

The granules obtained by the process of the invention are in a matrix form, that is to say the active principle particles are joined to one another via the binder, these particles thus being in the pendulous and funicular state and at the limit of a capillary state (Granulation Sherrington & R. Oliver, Heyden & Son, p. 7–18, 1981).

According to one method of implementation, the mass to be extruded is forced, after heating to above the melting point of the binder, through an extruder fitted with one or more dies having the diameter of the desired final granule. The extruded products at the outlet from the die are cut if necessary by means of a rotary cutter.

Extrusion by the molten route has the advantage over the processes of the prior art of preventing the at least partial solubility of the active principle in water, which solubility tends to modify the behaviour of the mass during extrusion. The conversion of the granules obtained by the process according to the invention to spheres is also facilitated, because the surface of the granule has plasticity characteristics owing to the surface melting of the binder, which characteristics did not exist in the granules obtained by the moist route. The granules obtained have, after conversion to spheres, a regular and smooth surface and thus require a much smaller amount of coating polymer for an equivalent effectiveness.

In comparison with the prior art, which uses moist route processes, the process of the present invention also has the advantage of avoiding the drying operations which lower the density of the granule (1.0 to 1.1 g/ml as compared with 1.2 g/ml for the granules of the present invention) by the formation of microporosity. The increase in density is important because it has been demonstrated that it was advantageous to have a minimum density of 1.2 in order to avoid the losses of active principles during mastication.

The moist route process was also highly sensitive to the mixing operation prior to the extrusion, in particular to the temperature and to the mixing time, although the molten route process according to the invention does not have this disadvantage.

The active principles are chosen from the amino acids, such as methionine, lysine or its salts, phenylalanine, histidine, arginine, tyrosine and tryptophan, and medicoments such as vitamins, antibiotics, anti-parasitic agents and proteins.

The granules obtained after a treatment for conversion to spheres, if necessary, are sieved to preserve a granule distribution of between 200 and 4000 μm and preferably between 500 μm and 2500 μm.

The coating layer, which provides protection against the rumen, is then sprayed in accordance with the technique described in the abovementioned US patents.

The coating contains at least one element which is chosen from polymers, copolymers or basic mixtures in which the proportion of nitrogen is between 2 and 14% and the molecular weight is between 50,000 and 500,000.

For the definition of the polymers and copolymers reference will be made to their definition in column 7 of U.S. Pat. No. 4,181,710, which is included in the present application by way of reference.

Amongst the copolymers, it is preferred to use the styrene/2-vinylpyridine copolymer (containing 50 to 80% by weight of 2-vinylpyridine and 20 to 50% of styrene).

The coating also contains a hydrophobic substance chosen from the fatty acids having 12 to 32 carbon atoms. They are also described in U.S. Pat. No. 4,181,710, which is also included in the present application by way of reference.

Amongst the hydrophobic substances, it is preferred to use stearic acid.

The preferred coating according to the invention has the following composition by weight:

10-30% of 2-vinylpyridine/styrene copolymer
70-90% of stearic acid.

The coating mixture containing the copolymer and the hydrophobic substance is dissolved in a halogenated solvent, an alcohol, an ether, a ketone or a mixture of these solvents. It is very particularly advantageous to use an ethanol/1,2-dichloroethane, ethanol/methylene chloride or ethanol/acetone mixture.

The solution of coating mixture is sprayed on the active principle cores, obtained by the process of the present invention, with the aid of a fluidized bed or any other spraying apparatus. For spraying, it is preferred to use an apparatus known under the name of spray-coating, for example of UNIGLATT type fitted with a WORSTER cell.

The amount of coating agent used, expressed as solids relative to the granule core, is in particular between 10 and 30% and preferably between 15 and 25%, this representing a coating thickness of between 20 and 70 μm for granules having an average diameter of between 500 μm and 1,600 μm.

The present invention will be described more fully with the aid of the following examples, which must not be regarded as limiting the invention.

EXAMPLE 1

1) Equipment Used

DITO SAMA planetary mixer
WYSS monoscrew extruder, diameter 35 mm, PHARMEX 35 T
feeding of the extruder via K TRON screw
variable speed granulator cutter having four flexible blades which rub against the die plate and the axis of which is on the axis of the screw
WYSS spheroniser, diameter 300 mm, SPHAEROMAT 300

2) Operating Conditions

| Extrusion: | |
|---|---|
| temperature of the double wall | 130° C. |
| speed of rotation of the screw | 150 rev/min |
| die: | |
| diameter of the orifice | 1.5 mm |
| inlet chamfer angle | 60° |
| length of the cylindrical channel | 3.5 mm |
| total thickness | 5 mm |
| number of orifices | 84 |
| Feed: | |
| delivery from the K-Tron screw adjusted to the extrusion delivery | |
| Cutting: | |
| axial, four-blade rotary cutter speed of rotation | 500 rev/min |
| Conversion to spheres: | |
| temperature of the double wall | 120° C. |
| speed of rotation of the plate | 1150 rev/min |

3) Preparation of the Mixtures

The binder is made up of pure stearic acid (UNICHEMA Prifrac 2981) and ethylcellulose (DOW 100). The initial mixtures are prepared by stirring for 15 minutes at ambient temperature by charging one kilo into a planetary mixer (DITO SAMA). The various constituents, methionine and binder, are introduced separately.

The average extrusion delivery is 6.25 kg/h and the particle size distribution of the product after converting to spheres is as follows:

| | diameter > 1,6 mm | 1% |
|---|---|---|
| 1.6 > | diameter > 1 | 92% |
| | diameter < 1 mm | 7% |

4) Variation in the Proportion of Binder

The proportion of binder in the final granule is varied between 10 and 11%, the binder consisting of a (94/6) stearic acid/ethylcellulose mixture. The results are given in Table I.

5) Variation in the Binder Composition

The relative proportion of stearic acid relative to the ethylcellulose is varied, keeping the proportion of binder at 11% by weight relative to the methionine. The results are given in Table II.

6) Conversion to Spheres

Experiments on conversion to spheres were carried out on methionine granulated with a proportion of 11% of binder consisting of 95% of stearic acid and 5% of ethylcellulose; the results are given in Table III.

EXAMPLE 2

Example 1 is repeated using the same equipment, the same operating conditions and the same binder, stearic acid/ethylcellulose in proportions by weight of 94/6, but using several mixtures of methionine and lysine in variable proportions as active material. The results of the experiments are given in Table IV.

EXAMPLE 3

Example 1 is repeated changing the nature of the meltable binder. The nature of the compositions which were the subject of extrusion is indicated in Table V. All of the products obtained underwent conversion to spheres without any problem.

TABLE I

| | | | | |
|---|---|---|---|---|
| Proportion of binder % of the granule | 11 | 10 | 10.5 | 11 |
| Average extrusion delivery kg/h | 6.31 | 6.45 | 6.00 | 6.25 |
| Particle size distribution of the core | | | | |
| diameter > 1.6 mm | 0 | 28 | 3 | 1 |
| 1.6 > diameter > 1 mm | 90 | 41 | 71 | 92 |
| 1 > diameter | 9 | 31 | 26 | 7 |
| Density | 1.24 | 1.23 | 1.22 | 1.24 |

TABLE II

| | | | | |
|---|---|---|---|---|
| Proportion of polymer % of the binder | 6 | 5 | 4 | 3 |
| Average extrusion delivery kg/h | 6.25 | 6.38 | 6.25 | 6.25 |
| Particle size distribution of the core | | | | |
| diameter > 1.6 mm | 1 | 1 | 71 | 1 |
| 1.6 > diameter > 1 mm | 92 | 89 | 25 | 86 |
| 1 > diameter | 7 | 10 | 4 | 13 |
| Density | 1.24 | 1.23 | 1.23 | 1.23 |
| Observation | | | Exudation and fouling of the die | |

| | | | |
|---|---|---|---|
| Proportion of polymer % of the binder | 2 | 1 | 0 |
| Average extrusion delivery kg/h | 6.00 | 6.38 | 6.50 |
| Particle size distribution of the core | | | |
| diameter > 1.6 mm | 12 | 4 | 11 |
| 1.6 > diameter > 1 mm | 80 | 86 | 82 |
| 1 > diameter | 8 | 10 | 7 |
| Density | 1.23 | 1.23 | 1.20 |
| Observation | Exudation and fouling of the die | | |

TABLE III

| | | | | |
|---|---|---|---|---|
| Time for conversion to spheres | 5 sec | 5 min | 10 min | 14 min |
| Particle size distribution of the core | | | | |
| diameter > 1.6 mm | 1 | 2 | 2 | 3 |
| 1.6 > diameter > 1 mm | 64 | 78 | 79 | 81 |
| 1 > diameter | 35 | 20 | 19 | 16 |
| Density | 1.22 | 1.23 | 1.25 | 1.25 |

TABLE IV

| | | | |
|---|---|---|---|
| Lysine hydrochloride (g) | 59 | 60 | 67 |
| Methionine (g) | 25.3 | 25.8 | 17 |
| Stearic acid (g) | 14.7 | 13.3 | 15 |
| Ethylcellulose (g) | 0.9 | 0.8 | 0.9 |
| Die in mm | 1.5 | 1 | 1.5 |
| Actual density | 1.21 | 1.22 | 1.21 |
| Particle size distribution | | | |
| diameter > 2 mm | 23 | 1 | 33 |
| 1.6 < diameter < 2 | 22 | 0 | 16 |
| 1.4 < diameter < 1.6 | 30 | 7 | 23 |
| 1.25 < diameter < 1.4 | 15 | 36 | 13 |
| 1 < diameter < 1.25 | 3 | 8 | 3 |
| diameter < 1 | 7 | 48 | 2 |

TABLE V

| Constituents | Fraction by weight | | | |
|---|---|---|---|---|
| Lysine.HCl | 63.75 | 63.75 | 63.75 | 63.75 |
| Methionine | 21.25 | 21.25 | 21.25 | 21.25 |
| Ethylcellulose | 1.05 | 1.05 | 1.05 | 1.05 |
| Stearic acid (1) | 8.37 | | | |
| Palmitic acid (1) | 5.58 | | | |
| Glycerol monostearate | | 13.95 | | |
| Glycerol distearate | | | 13.95 | |
| Hydrogenated tallow | | | | 13.95 |

We claim:

1. A process for making a coated granule having a minimum density of about 1.2 g/ml which contains an active principle selected from the group consisting of medicaments and amino acids intended for feeding ruminants comprising;
   extruding a dry mass of the active principle in the presence of a meltable binder in a molten state in an amount of less than 25% by weight, but in an amount sufficient to permit passage of the mixture of at least the active principle and meltable binder through a die; and coating the extruded core with a protective agent.

2. The process according to claim 1, characterized in that the principle is an amino acid selected from the group consisting of methionine and lysine hydrochloride.

3. The process according to claim 1, characterized in that the meltable binder is selected from the group consisting of polyethylene waxes, paraffins, oils and fats, which may be hydrogenated, fatty acids having 10 to 32 carbon atoms and the corresponding esters and alcohols of the fatty acids.

4. The process according to claim 3, characterised in that the meltable binder is stearic acid.

5. The process according to claim 1, characterised in that a sufficient amount of a polymer is added to obtain a mass permitting correct passage through the die and not causing exudation phenomena during extrusion.

6. The process according to claim 5, characterized in that the polymer is selected from the group consisting of the copolymers of styrene with vinylpyridines, alkylcelluloses, hydroxyalkylcelluloses, polyvinylpyrrolidones and polyethylenes.

7. The process according to claim 6, characterized in that the polymer is a copolymer composed of styrene and vinylpyridine.

8. The process according to claim 6, characterized in that the polymer is ethylcellulose.

9. A process for making a coated granule which contains an active principle selected from the group consisting of medicaments and amino acids intended for feeding ruminants comprising;
   extruding a dry mass of the active principle in the presence of a meltable binder in a molten state in an amount of less than 25% by weight, but in an amount sufficient to permit passage of the mixture of at least the active principle and meltable binder through a die; and
   coating the extruded core with a protective agent.

* * * * *